United States Patent
Riihimaa

(10) Patent No.: US 11,291,193 B2
(45) Date of Patent: Apr. 5, 2022

(54) CHAMBER FOR GROWING INVERTEBRATES

(71) Applicant: Entoprot Oy, Oulu (FI)

(72) Inventor: Ari Riihimaa, Oulu (FI)

( * ) Notice: Subject to any disclaimer, the term of this patent is extended or adjusted under 35 U.S.C. 154(b) by 236 days.

(21) Appl. No.: 16/300,669

(22) PCT Filed: May 18, 2017

(86) PCT No.: PCT/FI2017/000009
§ 371 (c)(1),
(2) Date: Nov. 12, 2018

(87) PCT Pub. No.: WO2017/198895
PCT Pub. Date: Nov. 23, 2017

(65) Prior Publication Data
US 2019/0297863 A1    Oct. 3, 2019

(30) Foreign Application Priority Data
May 20, 2016    (FI) .................................. 20160135

(51) Int. Cl.
*A01K 67/033*    (2006.01)
(52) U.S. Cl.
CPC ........ *A01K 67/033* (2013.01); *A01K 67/0332* (2013.01)
(58) Field of Classification Search
CPC .............. A01K 67/033; A01K 67/0331; A01K 67/0332; A01K 67/0333; A01K 67/0334; A01K 67/0335; A01K 67/0336; A01K 67/0337; A01K 67/0338; A01K 67/0339; A01K 67/04

USPC .......................................................... 119/6.5
See application file for complete search history.

(56) References Cited

U.S. PATENT DOCUMENTS

| 3,687,110 A | * | 8/1972 | Braunhut ............. A01K 67/033 |
| | | | 119/6.5 |
| 4,334,498 A | | 6/1982 | Bedding |
| 2015/0296760 A1 | | 10/2015 | Perednia |

FOREIGN PATENT DOCUMENTS

| CN | 202 907 656 | | 5/2013 | |
| FR | 473 763 A | | 1/1915 | |
| FR | 473763 A | * | 1/1915 | ........... A01K 67/033 |
| RU | 2005 363 C1 | | 1/1884 | |
| WO | WO-2013048546 A1 | * | 4/2013 | ............ C12M 41/48 |

OTHER PUBLICATIONS

European Search Report for EP17798811.0.
(Continued)

*Primary Examiner* — Brady W Frazier
(74) *Attorney, Agent, or Firm* — Jacob Eisenberg

(57) ABSTRACT

In the invention the growing surface of an apparatus for growing invertebrates is increased by a body or bodies (202) located in a growing chamber (201). When food is added to the growing chamber it is spread over at least some of the surfaces of bodies and the inner wall (203) of the growing chamber. This means that the area where invertebrates can grow is increased. The body or bodies are movable with respect to the inner wall of the growing chamber. This allows mixing the added food and other compounds in the growing chamber and it keeps air routes between bodies open.

4 Claims, 4 Drawing Sheets

(56) References Cited

OTHER PUBLICATIONS

Figure 1:
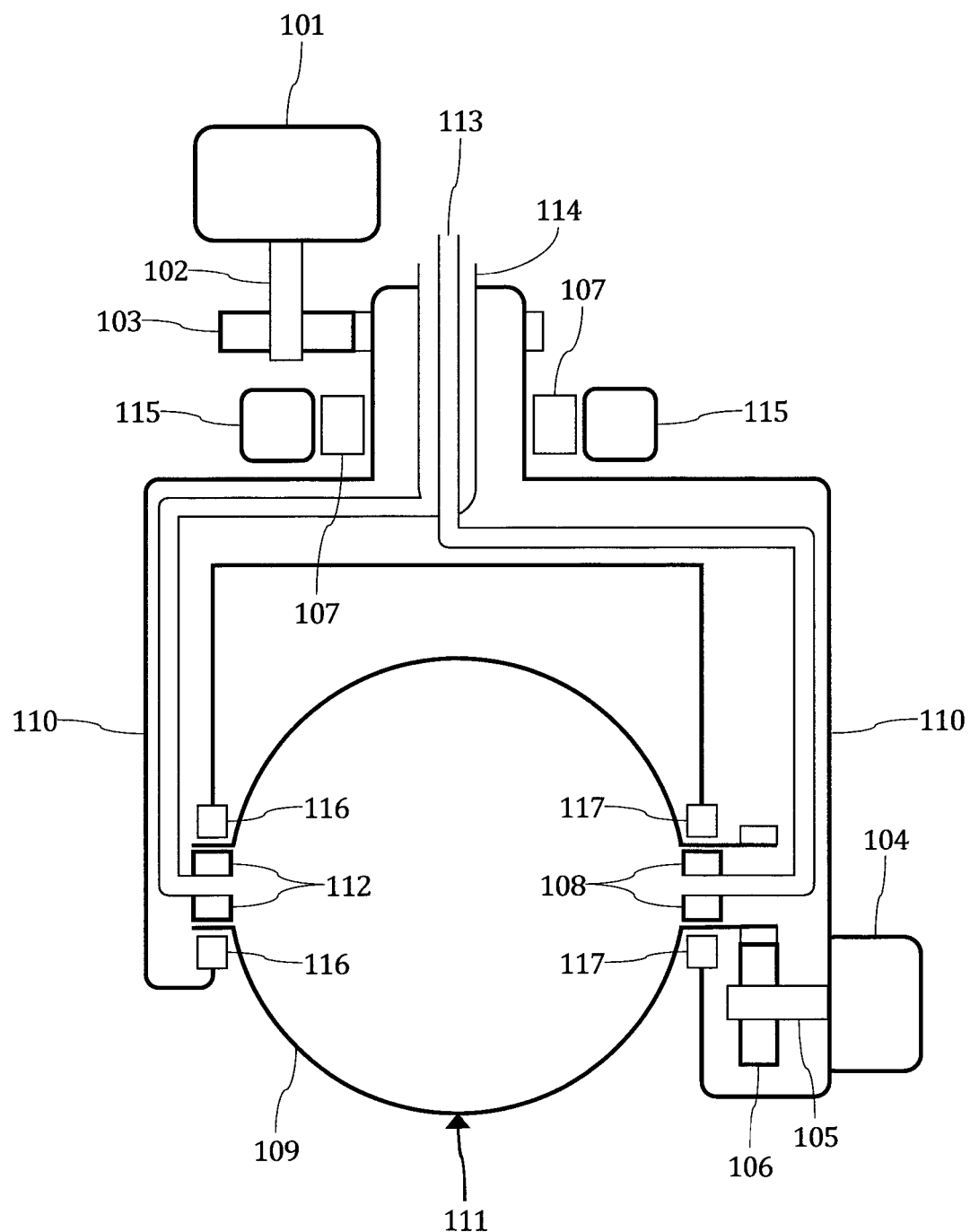

English Abstract for CN 202 907 656 U (Univ Southwest) May 1, 2013 (May 1, 2013).
Machine Translation of FR 473 763 A.
Machine Translation RU 2005 363 C1.

* cited by examiner

CHAMBER FOR GROWING INVERTEBRATES

The invention relates to an apparatus for growing invertebrates comprising a growing chamber which has an inner wall or similar arrangement for limiting the movements of the invertebrates, and a method for growing invertebrates.

BACKGROUND

Many invertebrates could be grown in artificial surroundings by placing them directly within a suitable food source. This food source is consumed by the invertebrates. When the invertebrates have grown enough they are removed from their growing space and are processed. The invertebrates, for example different kinds of larvae or worms, can be used in many ways. One possibilty is to use them as a protein source for animals or humans. This could be quite beneficial because many invertebrates have the ability to consume a wide range of organic materials and convert them into invertebrate matter. This process is quite efficient, and opens up many possibilities. However, there have been as of yet only a few attempts to do this on an industrial scale.

The conventional methods for growing invertebrates for example such as insect larvae have typically involved the use of flat trays or similar vessels. One example is disclosed in the patent publication US 2013/0319334. In this patent larvae are placed in the trays and food is added to the surface of the food mass and larvae. Because many invertebrates must have an adequate supply of air they tend to stay near the surface of the food layer. Even if the invertebrate to be grown is an anaerobic variety the heat inside the food mass could grow too high for the invertebrate to flourish. Also there could be many unwanted processes in the food layer areas without air such as fermentation. This means that to allow effective feeding and growth the food layer must not exceed some height that depends on the composition of the food matter and the abilities and traits of the invertebrates. This also means that to achieve optimal or near-optimal growing conditions, only a certain maximal number of invertebrates can be grown per a certain area of the growing chamber or other surface on which the mass of food and invertebrates reside during the growing process. Attempts have been made to circumvent these problems by introducing methods to mix the food layer for example by turning or moving the trays or containers. However even using such a method will not eliminate areas that are not optimal for the invertebrate to grow if the food layer is too thick.

BRIEF DESCRIPTION

The object of the invention is a solution that can significantly reduce the disadvantages and drawbacks of the prior art. In particular, the object of the invention is a solution that allows growing invertebrae on a commercial scale.

The objects of the invention are attained with an arrangement that is characterised by what is stated in the independent patent claims. Some advantageous embodiments of the invention are disclosed in the dependent claims.

In the invention the growing surface of an apparatus for growing invertebrates is increased by a body or bodies located in a growing chamber. When food is added to the growing chamber it is spread on at least some of the surfaces of bodies and the inner wall of the growing chamber. This means that the area where invertebrates can grow is increased. The body or bodies are movable with respect to the inner wall of the growing chamber. This allows mixing the added food and other compounds in the growing chamber and thus prevents food layers becoming too thick.

The invention is especially suitable for invertebrates that need air or inverterbrates having a larvae stage or being wormlike, but it is also applicable to other kinds of invertebrates. By 'needing air' it is meant here that the invertebrates breathe gas i.e. their respiratory systems are not suitable for liquid environments. If that kind of animal is submerged in liquid it will drown. Invertebrate groups that are suitable for growing with the invention, but are not limited to these, are arthropods, rheumatoid worms and nematodes. It must be noted that 'growing' is not limited to whole life span of an invertebrate but it could include one or more life stages or part of them. An example of this is the larval stages of a fly.

When reference is made in the text to the upper or the lower parts or respective directions, a situation is described in which the apparatus according to the invention is in its normal deployed configuration.

In one embodiment of the invention an apparatus for growing invertebrates comprise a growing chamber which has an inner wall or similar arrangement for limiting the movements of the invertebrates. In one advantageous embodiment of the invention there are one or more bodies inside the growing chamber for increasing the inner surface area of the growing chamber and the said body or bodies are configured to be movable with respect to the inner wall or similar arrangement. The apparatus further comprises a rotating mechanism for rotating the growing chamber, and the body or bodies are configured to move freely when the growing chamber is rotated and the growing chamber and the body or bodies are configured to have spaces for air between the body and the inner wall or between the bodies and the inner wall when food is spread at least partly on the surfaces of the body or the bodies and the inner wall. The inner wall and similar arrangements are for guiding or limiting the movements of the invertebrates. The increased surface area means that a larger amount of food can be spread per certain area or volume of the growing chamber in a manner that does not have the disadvantages that were described earlier. Advantageously the body or bodies can be arranged in a way that when a suitable amount of food is spread on the them there remains spaces for air or air flow that can pass through the contents composed of bodies, food and invertebrate. The arrangement can be such that there is a possibility to mix the said contents of the growing chamber. It must be noted that rotating does not mean that the growing chamber must make full turns. It can also change directions and stop after movements.

In one embodiment of the apparatus according to the invention, the bodies are at least partly spherical. In a second embodiment of the invention the minimum diameter of the bodies is 5 millimeters. In that case there still routes for the invertebrae remain between the bodies. Having spherical bodies also allows smoother movements of the bodies.

In a third embodiment at least some of the bodies have grooves, holes or protrusions or any combinations of thereof. In a fourth embodiment of the apparatus according to the invention, at least some of the protrusions are flexible. These shapes increase further the surface area over which food can be spread.

In a fifth embodiment of the apparatus according to the invention, there is a rotating mechanism for rotating the body or bodies. In a sixth embodiment of the apparatus according to the invention the rotation or the movement of the growing chamber is such that the average moving speed of the body or the bodies is slower than the moving speed of the invertebrates in the growing chamber. In other words the rotating mechanism for rotating the growing chamber or the rotating mechanism for rotating the body or bodies or combination of both is arranged to rotate the growing chamber or the body or bodies with respect to each other or to the inner wall of the growing chamber or to other means or arrangement set to guide or limit the movements of the invertebrates are mainly slower than the movement speed of the invertebrates that are meant to be grown in the growing chamber.

In a seventh embodiment of the apparatus according to the invention, air or other gas is arranged to be blown into the growing chamber in a way that gas flow is blowing over least some part of the surface of the body or bodies.

In an eighth embodiment of the apparatus there is at least one mixing arrangement which is fixed to the inner wall of the growing chamber.

In a ninth embodiment of the apparatus according to the invention, the body or the bodies are made wholly or partially of a material that serves as food for the invertebrates or for microorganisms that are part of the growing procedure, or contains chemicals or biologically active substances such as antibiotics, hormones or vitamins for the invertebrate or microorganisms.

A method for growing invertebrates that breathe gas according to an embodiment uses steps where food is fed into growing chamber which is at least partly filled with body or bodies movable in respect to inner wall or similar arrangement of said growing chamber and body or bodies are for increasing the inner surface area of the growing chamber and the growing chamber or body or bodies or both are rotated so the food will spread at least partly on the surfaces of the bodies and the inner wall of the growing chamber. The method further comprises a step where the invertebrates to be grown are added into the growing chamber before, during or after adding the food. In the method the apparatus described previously is used.

It is an advantage of the invention that it increases the amount of the invertebrates that can grown in a certain volume of a growing chamber compared to the conventional methods. The means that the invention makes it possible to use the floor area or 3-dimensional space of the production facility efficiently.

It is a further advantage of the invention that less manual labour is needed.

It is a further advantage of the invention that it improves the growing process. It also prevents anaerobic areas in the food layer. It is easier to arrange the measurement and adjustment of various environmental variables such as temperature and concentrations of chemical substances and gases. Also heat control and washing the growing chamber and its contents is easier.

It is a further advantage of the invention that it removes the need for constant observation.

An advantage is also that the invention can easily be modified for different species of invertebrates that require different growing conditions.

DESCRIPTIONS OF THE FIGURES

Figure 2:
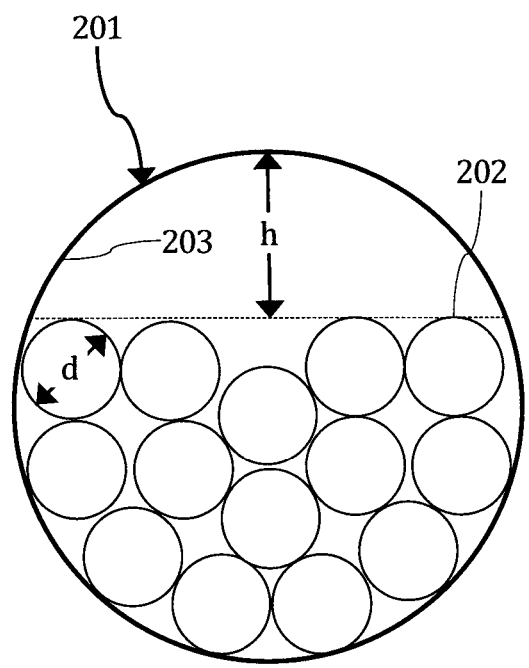
Figure 3:
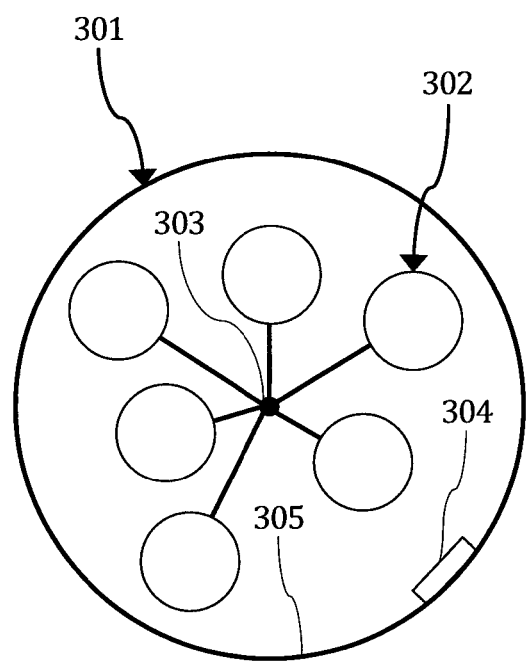
Figure 4:
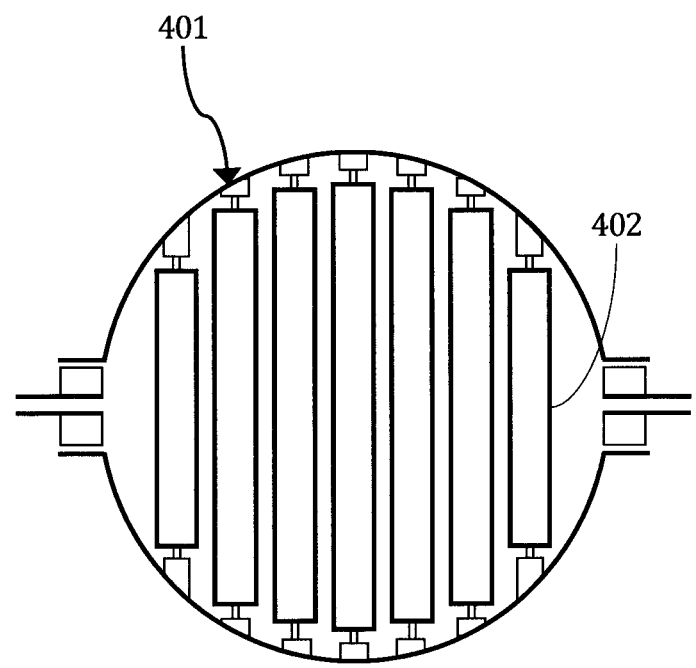
Figure 5:
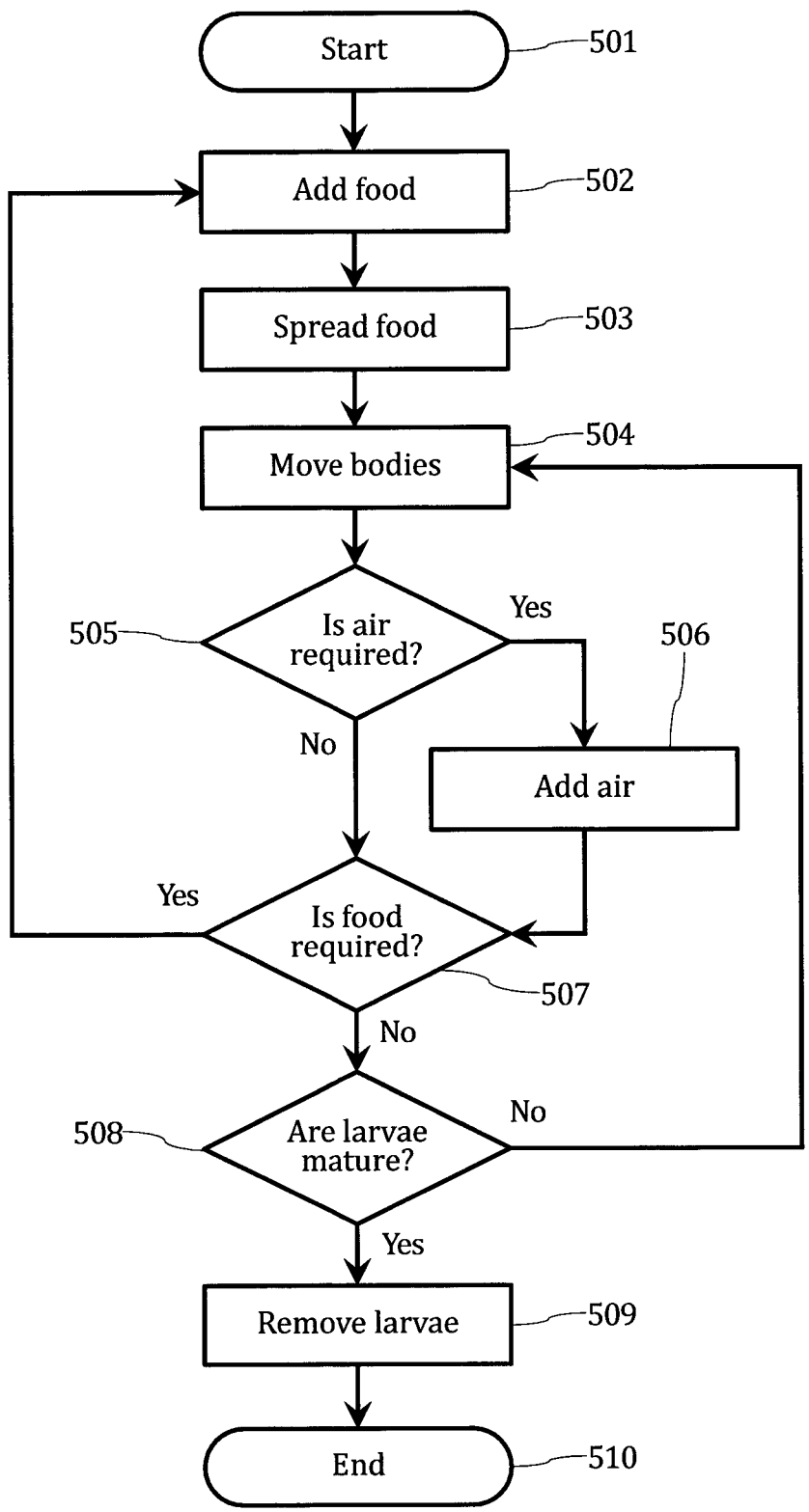

In the following, the invention is described in detail. The description refers to the accompanying drawings, in which FIG. 1 shows an example of an apparatus according to the invention, FIG. 2 shows a cross section of a growing chamber according to the invention, FIG. 3 shows another cross section of a growing chamber according to the invention, FIG. 4 shows a third cross section of a growing chamber according to the invention, and FIG. 5 shows an example of a method according to the invention as a flow chart,

DETAILED DESCRIPTIONS OF THE FIGURES

The embodiments in the following description are given as examples only and someone skilled in the art can carry out the basic idea of the invention also in some other way than what is described in the description. Though the description may refer to a certain embodiment or embodiments in several places, this does not mean that the reference would be directed towards only one described embodiment or that the described characteristic would be usable only in one described embodiment. The individual characteristics of two or more embodiments may be combined and new embodiments of the invention may thus be provided.

FIG. 1 shows a schematic cross-section of an apparatus 100 in accordance with an embodiment. The apparatus is viewed from above. In the apparatus is a growing chamber 111, a frame 115 and a forklike arrangement 110. The apparatus comprises also a first pipe 113 and a second pipe 114 for bringing material to the growing chamber and removing it. For moving the growing chamber and the forklike arrangement the apparatus comprise a first motor 101, a first axis 102, a first cogwheel 103, a second motor 104, a second axis 105 and a second cogwheel 106. The apparatus comprises also a bearing 107, a first growing chamber bearing 116 and a second growing chamber bearing 117.

The forklike arrangement 110 is attached to the frame 115 by the bearing 107. The forklike arrangement has two handles and the growing chamber 111 is attached between said handles by the first growing chamber bearing 116 and the second growing chamber bearing 117. The first growing chamber bearing is on one handle and the second growing chamber bearing is on another handle. The forklike arrangement can be rotated with the bearing 107. The growing chamber can be rotated with the first growing chamber bearing 116 and the second growing chamber bearing 117. The first motor 101 turns the first axis 102 and the first cogwheel 103 that is fixed to the first axis. The first cogwheel is arranged to rotate the forklike arrangement. The second motor 104 turns the second axis 105 and the second cogwheel 106 that is fixed to the second axis. The second cogwheel is arranged to rotate the growing chamber. By combining the movements caused by the first motor and the second motor, the growing chamber can be rotated or turned various ways or moved to a desired position.

The first pipe 113 and the second pipe 114 are situated inside the handles of the forklike arrangement 110. The first pipe is inside one handle and the second pipe is inside another handle. The first pipe brings food, air or washing fluid into the growing chamber 111. The second pipe removes used air or washing fluid from the growing chamber. There are a first locking element 108 and a second locking element 112. The first locking element is arranged to close the route from or to the first pipe to the growing chamber and the second locking element is arranged to close the route from or to the second pipe. The locking elements could also include sieve arrangements to prevent the invertebrates from escaping.

The growing chamber is a construct that guides and/or limits the movements of the living organisms during the growing process. In this embodiment the growing chamber 111 is a spherical construct. In the outer wall 109 of the growing chamber could be hatches or windows for inspection the inside of the growing chamber or other maintenance duties. The invertebrates to be grown are placed inside the growing chamber. This can be done for example through said hatch or the first pipe 113. In this example the growing chamber is mainly closed except the openings for the first pipe and the second pipe and maybe hatches and windows. This makes it possible to rotate and move the growing chamber in all directions and to all positions while the invertebrates cannot escape or fall out. Also the microbiological control of the growing chamber is easier when it is closed. Of course, the growing chamber could be constructed in a way that it is partly open. For example the growing chamber could be throughlike or there are one or more openings in the outer wall. The growing chamber contains walls or other structures, means or arrangements that guide or limit the movements of the invertebrates to be grown and keep them inside the growing chamber that keep the invertebrates to be grown inside the growing chamber until they are to be removed. If the growing chamber is open and if the growing chamber is arranged to be rotated or otherwise moved during the growing process, the movements must be such that the invertebrates to be grown do not fall out or escape. In addition to the physical structure comprising the walls of a growing chamber the inner walls or parts of them could be implemented with for example air currents, chemical differentials, electric fields, centrifugal forces or combination of different methods guiding or limiting the active or passive movements of the invertebrates. Examples of growing chambers are plates, trays, various vessels, and containers horizontal cylinders, troughs, conveyor belts, and bags. A growing chamber could be constructed from rigid or flexible or net-like material.

Inside the growing chamber 111 are placed a body or bodies (not shown in this figure). The body or bodies are for increasing the surface area where the food added into the growing chamber could attach. This means that the area of the food that is accessible for the invertebrates to be grown is increased significantly compared to the growing chamber without the bodies. The body or bodies are arranged to movable with respect to the inner wall of the growing chamber. This means that the food and other matter inside the growing chamber can be mixed. Also the body or the bodies provide spaces for air between them and the inner wall. This same space or spaces can be used by the inverterbrates for moving. The movements of the body or bodies with respect to the inner wall of the growing chamber can be implemented in various ways. For example the body or bodies can be unattached bodies that move freely inside the growing chamber when the growing chamber is rotated or moved. The body or bodies can also be attached to a shaft or axis which is rotated. This means that it is not always necessary to move or rotate the growing chamber in order to move the body or bodies with respect to each other or the inner wall. The size of the body or the bodies depend the properties of the food and the physical needs of inverterbrates.

FIG. 2 shows a cross section of a growing chamber 201 in accordance with an embodiment. In this example there are several bodies 202 inside the growing chamber. The bodies are unattached and are free to move. The bodies are spherical having diameter d. Naturally, the bodies can be different in size. The bodies fill the growing chamber in a way that there is a free space in the upper part of the growing chamber. The height of the free space is h. This is from the upper level of the bodies to the highest point of the growing chamber. The growing chamber has an inner wall surface 203 that is spherical. As the growing chamber is rotated the bodies roll and mix the food and spread it on the surface of the bodies. The food is also spread on the inner wall of the growing chamber. The growing chamber can be rotated for example in a way that was described in the embodiment presented in the FIG. 1. Advantageously the rotation or the movement of the growing chamber is such that the average moving speed is slower than the moving speed of the invertebrates in the growing chamber. This means that the average moving speed of the body or the bodies is slower than the moving speed of the invertebrates. The diameter d is chosen so that there is space at least for the inteverberates to be grown between the bodies that are at least partly covered with the food. If the inteverberates to be grown requires air there should also be space for air. The minimum diameter is 5 mm. For improving the air circulation between the bodies air can be led among the bodies. Air currents and movement of the bodies keep the routes between the bodies open. Air currents also lead the excess heat away.

By having the spherical inner wall 203 diminishes the possibility that the bodies get stuck to each other. The shape of the inner wall could also be different.

The material of the bodies 202 could be some light material. The bodies can also be hollow. When the bodies are light weight they can be moved by the air currents that are led into the growing chamber. The body or bodies could have grooves, holes or protrusions or any combinations of thereof. These increases further the area that could be covered by the food. The protrusions could be rigid or flexible.

FIG. 3 shows a cross section of a growing chamber 301 according to another embodiment. The growing chamber has an inner wall 305. Inside the growing chamber is a body 302 that is rotatable by an axis 303. The body comprises many protrusions that are fixed to the axis. In this example the protrusions are shafts having spherelike objects attached to them. The lengths of the shafts vary. This means that the distances of the spherelike objects from the inner wall also vary. It must be noted that this is a simplified example of a one body embodiment. It could be implemented in various ways. Also it must be noted that the axis need not to be in the center of the growing chamber. Further it must be noted that in a case of having one body inside the growing chamber, the body needs not be attached anywhere but it could be freely movable like the bodies in the embodiment of FIG. 2. On the inner wall 305 is fixed a mixing arrangement 304. When the growing chamber turns, the mixing arrangement mixes the material inside the growing chamber. In this example the mixing arrangement is such sized that it does not touch the bodies. In some embodiment the mixing arrangement could be used for moving the bodies such are presented in FIG. 3. In that case the mixing arrangement both mixes materials and moves the bodies. However, using free moving bodies inside the growing chamber diminish the need of the mixing arrangements.

FIG. 4 shows a cross section of a growing chamber 401 according to another embodiment. Inside the growing chamber are bodies 402 that are cylindrical. Both ends of the cylinders are connected to the inner wall of the growing chamber in a way that the cylinders are rotatable around theirs longitudinal axis. The cylinders could have flexible protrusions.

Also one variation of the arrangement of the bodies could be an embodiment that is similar that the embodiment in FIG. 2 but now at least some of the bodies are connected to the inner wall of the growing chamber with some flexible means. This could be for example some beltlike arrangement. When the growing chamber rotates the beltlike arrangements lift and move bodies that they are connected to. This enhances the mixing of the food and the bodies.

In one embodiment there is a mixing arrangement that is fixed to an inner wall of a growing chamber. The mixing arrangement could be implemented in various ways. It could comprise one part or many separate parts. For example it could be a plow-like or flangelike arrangement. When the growing chamber is rotated the mixing arrangement mixes the matter inside the growing chamber like for example the food and/or the bodies.

In FIG. 5 is disclosed a flow chart describing an example of a method for growing invertebrates using the invention.

In the method an apparatus according the invention is used. In this example the invertebrates to be grown are larvae of the housefly (order Diptera, *Musca domestica*). If some other species of invertebrate is used the steps could be different.

The method for growing invertebrates is started at the step 501.

At the step 502 a liquid food medium is added to the growing chamber. The food medium is for example a mixture of solid food matter and water. The amount of food is such that when it is spread on the bodies in step 503 there still remain spaces for air or air flow through the contents composed of body or bodies, food and larvae. The young larvae are mixed in said liquid food medium when the food is added for the first time in the growing process.

At the step 503 the growing chamber is rotated in a way that the liquid food medium spreads evenly over the bodies inside the growing chamber.

At the step 504 the growing chamber is rotated or moved in a way that bodies will move and the food medium and other materials inside the growing chamber are mixed and spread on the surface of the body or bodies. Also the spaces between the bodies will be open due to these movements. This step can also be implemented by moving the body or the bodies or moving both the body or the bodies and the growing chamber.

At the step 505 it is checked if breathing air is needed. If the air should be changed, it is done at the step 506.

At the step 506 the breathing air is changed in the growing chamber. New air is blown to the lower part of the growing chamber among the bodies. The oxygen-rich air flows between the bodies. The used air is removed from the upper part of the growing chamber. It must be noted that if the growing chamber is arranged to be rotated the airing process is done when the inlet and outlet holes for air are in a suitable position. Airing can be done also in different ways.

If the air does not need to be changed at the step 507 it is checked if more food is needed. If more food is required, it is done at the step 502.

If no food or air is required, at the step 508 is checked if the larvae have matured to the desired size. When the larvae are mature they are removed from the growing chamber by leading water into the growing chamber and flushing it through outlet hole at the step 509.

If the larvae are not mature, the growing chamber is rotated in a way that the bodies move in respect to the inner wall of the growing chamber. The movement is such that the spaces between the bodies will remain at least partly open. This is done at the step 504.

At the step 510 the method for growing invertebrates is ended.

It must be noted that the previous steps could be executed in a different order or some steps are executed simultaneously. Naturally the method could include steps that are not described here like for example washing the interior of the growing chamber during the growing process. Also many steps could be implemented differently when growing different species or using a different apparatus.

Some advantageous embodiments of the method and device according to the invention have been described above. The invention is however not limited to the embodiments described above, but the inventive idea can be applied in numerous ways within the scope of the claims.

The invention claimed is:

1. An apparatus for growing invertebrates that breathe gas, the apparatus comprising:
   a growing chamber comprises an inner wall arranged and configured for limiting movements of invertebrates,
   wherein an inside of the growing chamber comprises an inner surface area,
   wherein a body or bodies are arranged inside the growing chamber and are configured for increasing the inner surface area,
   wherein the body or bodies are further configured to be movable with respect to the inner wall,
   a rotating mechanism for rotating the growing chamber,
   a first pipe configured and arranged to introduce at least one of air and another gas into the growing chamber in such a manner that the at least one of air and another gas flow is capable of tracing at least some part of the surface of the body or bodies, and
   a second pipe configured and arranged to remove at least one of air, another gas and washing fluid from the growing chamber,
   wherein the body or bodies are configured to move freely when the growing chamber is rotated, and
   wherein the growing chamber and the body or bodies are further configured to define spaces for air, the spaces arranged between the body and the inner wall of the growing chamber or between the bodies and the inner wall of the growing chamber when food is spread at least partly on surfaces of the body or bodies and the inner wall.

2. The apparatus according to claim 1, wherein the body or bodies are at least partly spherical.

3. The apparatus according to claim 2, wherein the minimum diameter of the bodies is 5 millimeters.

4. The apparatus according to claim 1, wherein the body or the bodies are made wholly or partially of a material that serves as food for the invertebrates or for microorganisms that are part of the growing procedure, or contains chemicals or biologically active substances such as antibiotics, hormones or vitamins for the invertebrate or microorganisms.

\* \* \* \* \*